US011455814B2

(12) United States Patent
Sridhar

(10) Patent No.: US 11,455,814 B2
(45) Date of Patent: Sep. 27, 2022

(54) DISTRACTED DRIVER DETECTION DEVICE

(71) Applicant: Ananya K. Sridhar, Richardson, TX (US)

(72) Inventor: Ananya K. Sridhar, Richardson, TX (US)

( * ) Notice: Subject to any disclaimer, the term of this patent is extended or adjusted under 35 U.S.C. 154(b) by 0 days.

(21) Appl. No.: 17/382,330

(22) Filed: Jul. 21, 2021

(65) Prior Publication Data

US 2021/0350121 A1 Nov. 11, 2021

(51) Int. Cl.
G06V 40/10 (2022.01)
G08B 7/00 (2006.01)
G08B 21/02 (2006.01)
B60Q 9/00 (2006.01)

(52) U.S. Cl.
CPC ............... *G06V 40/10* (2022.01); *G08B 7/00* (2013.01); *G08B 21/02* (2013.01); *B60Q 9/008* (2013.01)

(58) Field of Classification Search
CPC ...... G06V 40/10; G06V 20/597; G06V 40/18; G08B 7/00; G08B 21/02; G08B 21/06; B60Q 9/008; A61B 5/002; A61B 5/0077; A61B 5/1103; A61B 5/1114; A61B 5/1121; A61B 5/163; A61B 5/165; A61B 5/168; A61B 5/746; A61B 2503/22; A61B 2576/02; A61B 5/18
See application file for complete search history.

(56) References Cited

U.S. PATENT DOCUMENTS 11,181,978 B2 * 11/2021 Li ........................... G06F 3/012
2019/0279009 A1 * 9/2019 Srirangam Narashiman ............... G06V 40/176

OTHER PUBLICATIONS

Friedrichs, et al., Camera-based Drowsiness Reference for Driver State Classification under Real Driving Conditions, 2010 IEEE Intelligent Vehicles Symposium; University of California, San Diego, CA, USA, Jun. 21-24, 2010.
Hossain, et al., IOT based Real-time Drowsy Driving Detection System for the Prevention of Road Accidents, ICIIBMS 2018, Track 1: Image Processing, Computer Science and Information technology, Bangkok, Thailand.
Sistla, et al., Stacked Ensemble Classification Based Real-Time Driver Drowsiness Detection, International Journal of Safety and Security Engineering, vol. 10, No. 3, Jun. 2020, pp. 365-371.
(Continued)

*Primary Examiner* — Quan Zhen Wang
*Assistant Examiner* — Rajsheed O Black-Childress
(74) *Attorney, Agent, or Firm* — Microelectronic Devices IP LLC; Shawn T. Walsh

(57) ABSTRACT

A distracted driver detection device for use in a vehicle includes a processor, a video camera, and an accelerometer. The processor is configured to compute an eye open ratio (EOR) and a mouth open ratio (MOR). The processor is configured to provide an audio alert signal to an audio alert component and provide a visual alert signal to a visual alert component when the EOR is less than an EOR threshold for a prescribed EOR assessment time, when the MOR is greater than the MOR threshold for a prescribed MOR assessment time, or when the estimate of the acceleration is greater than an acceleration threshold. The EOR and MOR are calculated from facial landmarks that are generated by a Histogram of Oriented Gradients (HOG) algorithm implemented by the processor.

18 Claims, 9 Drawing Sheets

(56) References Cited

OTHER PUBLICATIONS

Jang et al., Implementation of Detection System for Drowsy Driving Prevention Using Image Recognition and IoT, Sustainability 2020, 12, 3037; doi:10.3390/su12073037.

Kashevnik, et al., Cloud-Based Driver Monitoring System Using Smartphone, IEEE Sensors Journal, This article has been accepted for publication in a future issue of this journal, but has not been fully edited. Content may change prior to final publication. Citation information: DOI 10.1109/JSEN.2020.2975382, IEEE Sensors Journal.

Xu et al., Sober Drive: A Smartphone-assisted Drowsy Driving Detection System, 2014 International Conference on Computing, Networking and Communications, Mobile Computing & Vehicle Communications Symposium.

\* cited by examiner

EXAMPLE FACE PATTERN GENERATED BY THE HOG ALGORITHM

EXAMPLE MAP OF FACIAL LANDMARKS

DISTRACTED DRIVER DETECTION DEVICE

FIELD

This disclosure relates to the field of devices for detecting distracted or impaired drivers. More particularly, but not exclusively, this disclosure relates to devices for detecting distracted or impaired drivers using aspects of facial recognition.

BACKGROUND

Distracted or impaired driving includes driving while drowsy or while using a cellphone. Distracted driving accounts for a significant fraction of all vehicle accident fatalities and is one of the leading causes of teen vehicle accidents. The National Highway Traffic Safety Administration estimated that in the years 2011-2015, there were 360,000 accidents, 160,000 injuries, and 3662 fatalities as a result of people falling asleep behind the wheel. The number of fatalities is believed to be significantly underestimated.

SUMMARY

The present disclosure introduces a distracted driver detection device for use in a vehicle, including a processor, a video camera which provides video input to the processor, and an accelerometer which provides acceleration input to the processor. The distracted driver detection device further includes a visual alert component, an audio alert component, and a wireless communication component. The visual alert component generates a visual alert to a driver upon receiving a visual alert signal from the processor. The audio alert component generates an audio alert to the driver upon receiving an audio alert signal from the processor. The wireless communication component provides a wireless message upon receiving a wireless alert signal from the processor.

The processor is configured to identify left and right eye shape structures of the driver using the video input. The processor is further configured to compute an eye open ratio (EOR) using the left and right eye shape structures. A low EOR, that is, below an EOR threshold, indicates the driver's eyes are closed or looking down, implying distracted driving. The processor is configured to provide the audio alert signal to the audio alert component, provide the visual alert signal to the visual alert component, and provide the wireless alert signal to the wireless communication component, when the EOR is less than the EOR threshold for a prescribed EOR assessment time.

Similarly, the processor is configured to identify a mouth shape structure of the driver using the video input. The processor is further configured to compute a mouth open ratio (MOR) using the mouth shape structure. A high MOR, that is, above an MOR threshold, indicates the driver's mouth is yawning, implying distracted driving. The processor is configured to provide the audio alert signal, provide the visual alert signal, and provide the wireless alert signal, when the MOR is greater than the MOR threshold for a prescribed MOR assessment time.

The processor is also configured to estimate an acceleration of the vehicle using the acceleration input. The processor is further configured to provide the audio alert signal, the visual alert signal, and the wireless alert signal, when the estimate of the acceleration is greater than an acceleration threshold.

The processor is moreover configured to accumulate an excursion count of EOR threshold excursions, MOR threshold excursions, and acceleration threshold excursions, and to report the excursion count using the wireless communication component when the excursion count exceeds a driver score limit in a prescribed time period.

DETAILED DESCRIPTION

Figure 1:
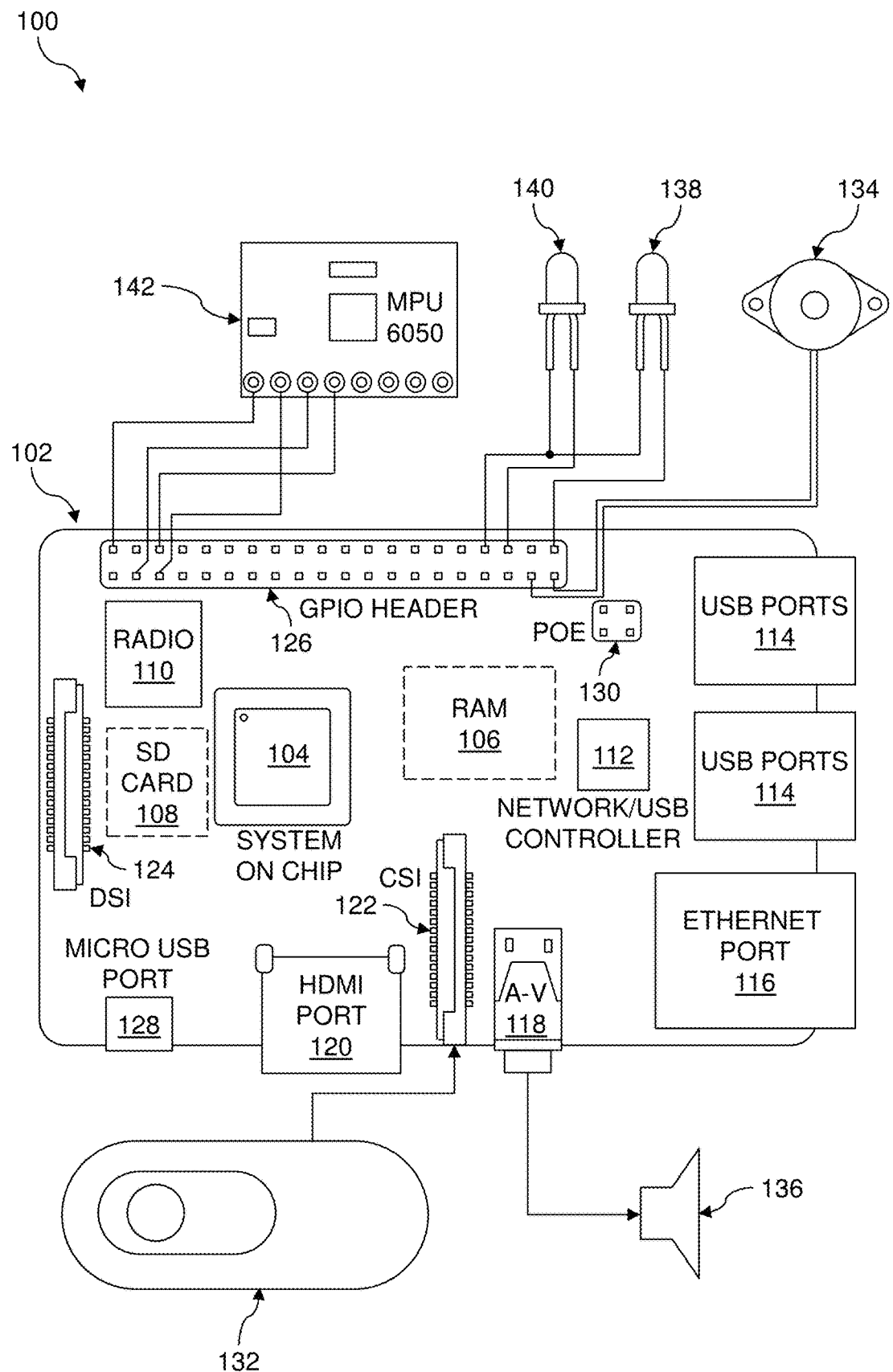
FIG. 1 is a schematic view of an example of the distracted driver detection device.

The present disclosure is described with reference to the attached figures. The figures are not drawn to scale and they are provided merely to illustrate the disclosure. Several aspects of the disclosure are described below with reference to example applications for illustration. It should be understood that numerous specific details, relationships, and methods are set forth to provide an understanding of the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

A distracted driver detection device for use in a vehicle is configured to provide audio and visual alerts to a driver of the vehicle when the distracted driver detection device determines indicators of distracted driving are occurring. The distracted driver detection device includes a processor, a video camera, and an accelerometer. The video camera provides video input of the driver's face to the processor. The accelerometer provides acceleration input to the processor.

For the purposes of this disclosure, the term "acceleration" is construed to include any change in velocity of the vehicle, and includes both positive change in velocity, that is, speeding up, and negative change in velocity, that is, slowing down. A negative change in velocity may be caused by braking or a collision, by way of example. The term "acceleration" is further construed to include lateral change in velocity, as may occur during turning or swerving.

The distracted driver detection device includes a visual alert component, which is configured to generate a visual alert to the driver upon receiving a visual alert signal from the processor. The visual alert may be implemented as a red light, either steady or blinking, within the driver's normal field of vision. The distracted driver detection device includes an audio alert component, which is configured to generate an audio alert to the driver upon receiving an audio alert signal from the processor. The audio alert may be implemented as a buzzer alert, or a voice alert, or both.

The processor is configured to use the video input from the video camera to generate coordinates of facial landmarks of the driver corresponding to eye shape structures and a mouth shape structure. The processor is further configured to compute an eye open ratio (EOR) using the eye shape structures, and to compute a mouth open ratio (MOR) using the mouth shape structure. The processor is also configured to estimate an acceleration of the vehicle using the acceleration input.

The processor is configured to accumulate an excursion count of EOR threshold excursions, MOR threshold excursions, and acceleration threshold excursions. The processor is further configured to report the excursion count using the wireless communication component when the excursion count exceeds a driver score limit in a prescribed time period.

FIG. 1 is a schematic view of an example of the distracted driver detection device. The distracted driver detection device 100 includes a processor 102. In this example, the processor 102 may be manifested as a Raspberry Pi 3 microcontroller, available from the Raspberry Pi Foundation. FIG. 1 shows a top side of the processor 102. The processor 102 includes a system on chip 104 which has a 64 bit 1.2 GHZ Quad Core ARM V8 central processing unit (CPU) and a graphics processing unit (GPU). The processor 102 includes a random access memory (RAM) 106, containing volatile memory, and a secure digital (SD) card 108, containing non-volatile memory, which are both located on an underside of the Raspberry Pi 3 microcontroller, in this example.

The processor 102 includes a wireless communication component 110, labeled "RADIO" in FIG. 1. The wireless communication component 110 enables communication over WiFi and Bluetooth channels. The processor 102 also includes a network and universal serial bus (USB) controller 112. The processor 102 further includes USB ports 114 and an Ethernet port 116. In this example, the processor 102 includes four USB ports 114. The network and USB controller 112 manages communications through the USB ports 114 and the Ethernet port 116 to the system on chip 104.

The processor 102 includes an audio/visual jack 118, labeled "A-V" in FIG. 1, a high definition multimedia interface (HDMI) port 120, for audio and video output from the system on chip 104. The processor 102 includes a camera serial interface (CSI) port 122, for video input from a camera to the system on chip 104. The processor 102 includes a display serial interface (DSI) port 124, for display output from the system on chip 104. The processor 102 includes a general purpose input/output (GPIO) port 126 having 40 pins for input and output of digital and analog signals.

The processor 102 includes two ports for power input: a micro USB port 128 and a power-over-Ethernet header 130, labeled "POE" in FIG. 1. The processor 102 may be powered through either of these two ports. When using the power-over-Ethernet header 130, voltage on the Ethernet line is commonly 48 volts, and must be stepped down to approximately 5 volts for active components of the processor 102.

The distracted driver detection device 100 includes a video camera 132 connected to the CSI port 122 of the processor 102. The video camera 132 provides video input of the driver's face to the processor 102 during operation of the distracted driver detection device 100. The video camera 132 is advantageously able to provide a sufficient image quality when the distracted driver detection device 100 is operated in low light or dark conditions, such as driving at night.

The distracted driver detection device 100 includes a first audio alert component, implemented as a buzzer 134 connected to the GPIO port 126 of the processor 102. The buzzer 134 is configured to generate a buzzer alert to the driver upon receiving a first audio alert signal from the processor 102 during operation of the distracted driver detection device 100. The distracted driver detection device 100 also includes a second audio alert component, implemented as a speaker 136 connected to the audio/visual jack 118 of the processor 102. The speaker 136 is configured to generate a voice alert to the driver upon receiving a second audio alert signal from the processor 102.

The distracted driver detection device 100 includes a visual alert component, implemented as a red light emitting diode (LED) 138 connected to the GPIO port 126 of the processor 102. The red LED 138 is configured to generate a visual alert, either a steady red light or a blinking red light, to the driver, within the driver's normal field of vision, upon receiving a visual alert signal from the processor 102. The distracted driver detection device 100 also includes a safe driving visual signal component, implemented as a green LED 140 connected to the GPIO port 126 of the processor 102. The green LED 140 is configured to generate a safe driving status signal to the driver, upon receiving a safe driving signal from the processor 102, signaling no indications of distracted driving.

The distracted driver detection device 100 includes an accelerometer 142 connected to the GPIO port 126 of the processor 102. The accelerometer 142 is configured to provide acceleration input to the processor 102 during operation of the distracted driver detection device 100. The accelerometer 142 may be implemented as a MPU-6050 accelerometer chip mounted on a fanout board, as indicated in FIG. 1.

The distracted driver detection device 100 may be initially configured by connecting the processor 102 to the Internet through the Ethernet port 116 and running command: $sudo raspi-config, followed by commands: $sudo apt-get update and $sudo apt-get upgrade.

Updates to a camera application on the processor 102 that supports the video camera 132 may be found online, by running command: $sudo rasp-config, which will display a list of updates, including a "camera" option. The "camera" option is selected and the update is finalized by selecting "Finish".

Initial configuration of the distracted driver detection device 100 is continued by installing Open-Source Computer Vision Library (OpenCV) in the SD card 108 of the processor 102. OpenCV provides a common open-source platform for computer vision applications. Since the Raspberry Pi has limited onboard memory, the swap space may be optimized to allow installation.

Figure 2:
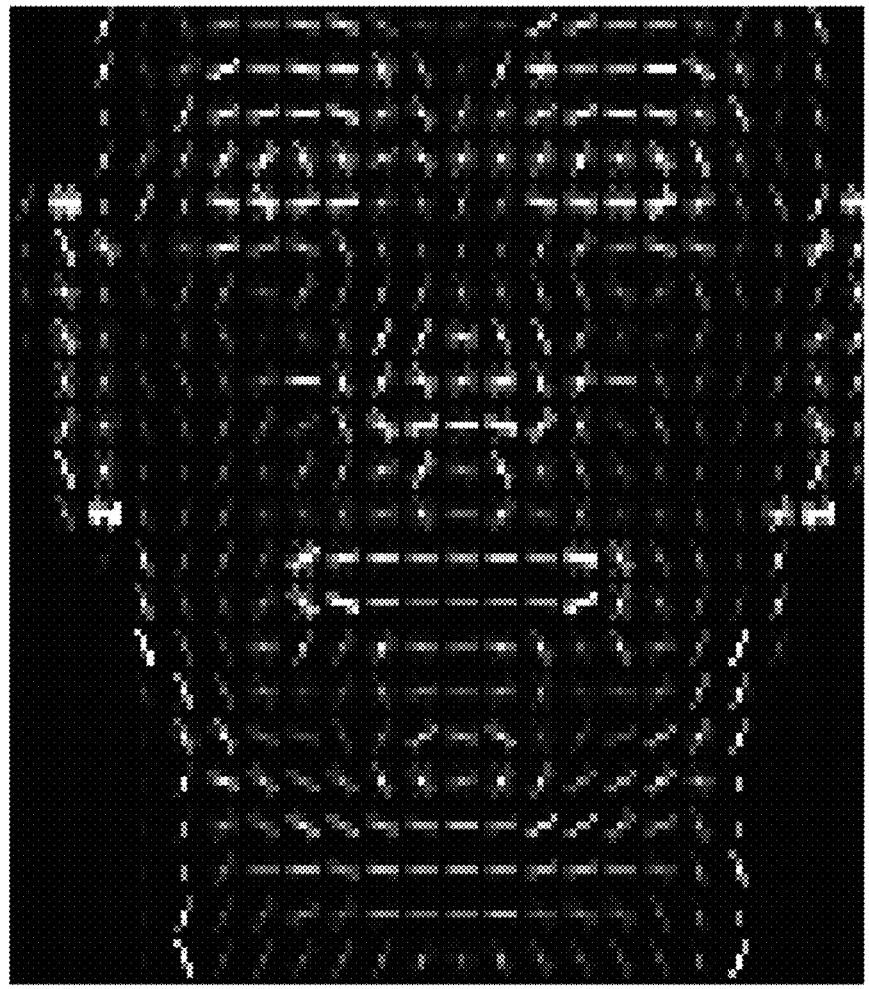
FIG. 2 depicts an example representation of facial features produced by the Histogram of Oriented Gradients (HOG) algorithm.

Following installation of OpenCV, general-purpose software library Dlib is installed in the SD card 108. Dlib is written in the programming language C++. Within Dlib, there is a facial recognition module. The facial recognition module uses 128 dimension (128-d) vectors that are representative of individual faces. The 128-d vectors are generated using the encode_faces.py routine, created by Adrian Rosenbrock of Raspberry PI foundation, in Dlib. The encode_faces.py routine uses a representation of facial features produced by a Histogram of Oriented Gradients (HOG) algorithm, developed by Paul Viola and Michael Jones in 2005, which is also available in Dlib. An example representation of facial features produced by the HOG algorithm is shown in FIG. 2. A directory of the 128-d vectors may be generated for one or more drivers of the vehicle, that is, know drivers, to enable driver recognition during operation of the distracted driver detection device 100. Specific values for the EOR threshold and the MOR threshold for the known drivers may also be stored, to provide more accurate assessments of distracted driving. The specific values for the EOR threshold and the MOR threshold may be generated by offline testing of the known drivers, or by a learning process during actual driving.

An image of one of the driver's face is used to produce the corresponding 128-d vector. The HOG algorithm starts by first calculating a horizontal gradient $g_x$ and a vertical gradient $g_y$ for each pixel of the image, using horizontal and vertical binary filters. The same results can also be achieved by using Sobel operator in OpenCV with kernel size 1. Next, a gradient magnitude, g, and direction angle, θ, are computed for each pixel using the following formulae:

$$g=\sqrt{g_x^2+g_y^2}$$

$$\theta=\arctan(g_y/g_x).$$

The image is then divided into small squares of 16×16 pixels each. For each small square, the HOG algorithm counts how many gradients point in each major direction, that is, a histogram of how many point up, point up-right, point right, etc. The histogram data for all the small squares of 16×16 pixels provide a face pattern that is then used to generate the 128-d vector. An example face pattern generated by the HOG algorithm is shown in FIG. 2.

Referring back to FIG. 1, OpenCV also includes a facial landmarks detector that scans in an image and is able to identify a face and describe it as a map of 68 coordinates of facial landmarks. The map of the 68 facial landmarks is rotated and stretched to center the landmarks. The centered landmarks are then used to generate the 128-d vector.

The facial landmarks coordinates are also used to calculate the EOR and MOR in real time using the video input from the video camera 132. OpenCV includes two routines for generating the facial landmarks coordinates: a first routine using the HOG algorithm and Linear Support Vector Machine (SVM) algorithm (the HOG+LinearSVM routine) in Dlib, and a second routine using a Haar cascade face detector. After some experimentation, it was determined that the Haar cascade routine was able to process the video input more quickly than the HOG+LinearSVM routine, and this routine is used in the distracted driver detection device 100. The video camera 132 is configured to provide 640×480 pixel frames at a frame rate of 20 video frames per second, which is sufficiently fast to detect indicators of distracted driving using the EOR and MOR, while enabling the facial landmarks detector to provide updated facial landmarks coordinates for each video frame. In other versions of the distracted driver detection device 100, the video camera 132 may be configured to provide a frame rate of 15 to 30 video frames per second. Future improvements in processing power of the processor 102 may enable frames with higher pixel count or faster frame rates.

Figure 3:
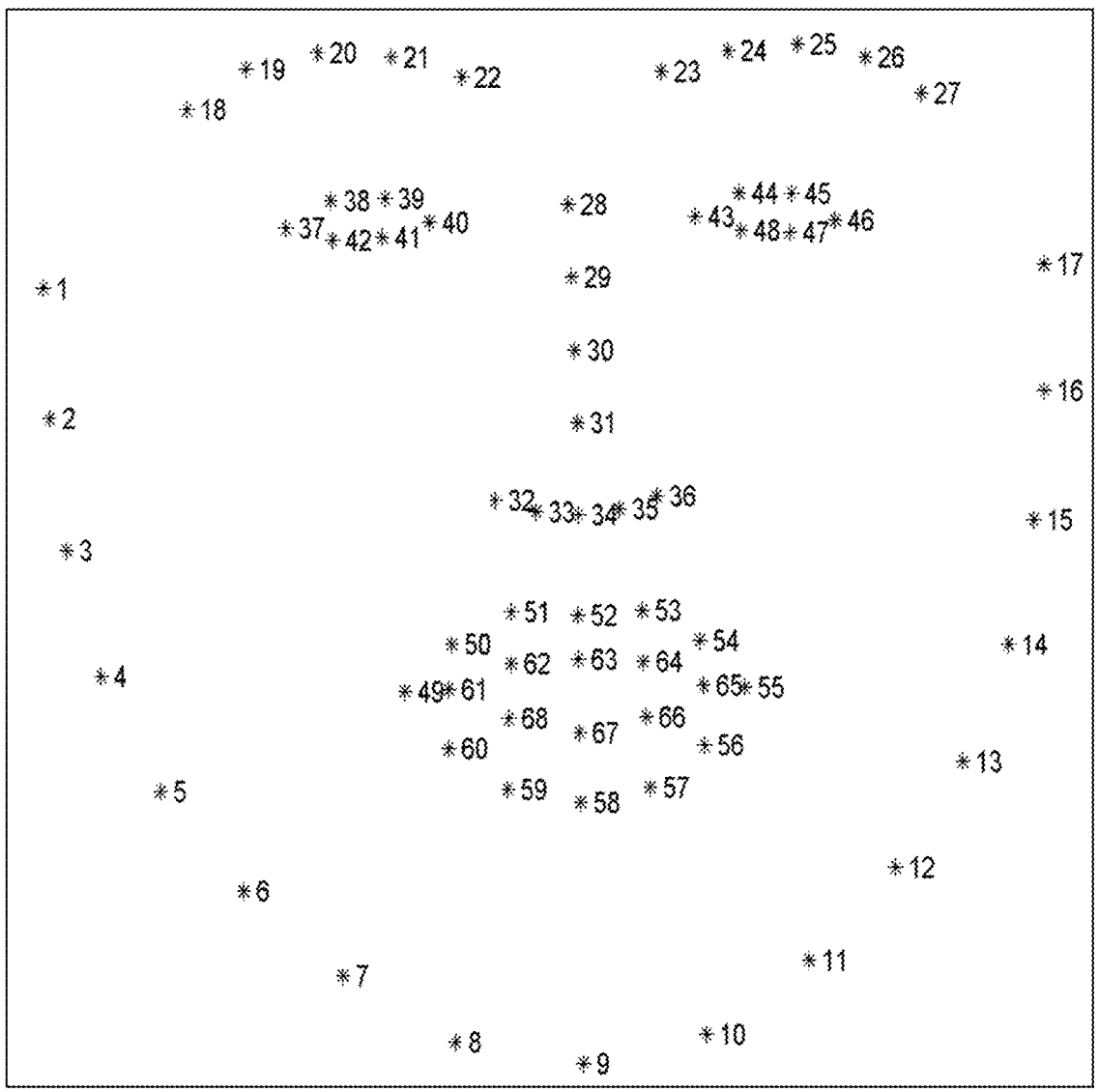
FIG. 3 shows an example map of the facial landmarks.

FIG. 3 shows an example map of the facial landmarks. Each of the facial landmarks, labeled 1 through 68, have x and y coordinates. Landmarks 37 through 42 provide a right eye shape structure. Landmarks 43 through 48 provide a left eye shape structure. Landmarks 49 through 68 provide a mouth shape structure.

The distracted driver detection device 100 is positioned in a vehicle, not shown, so that the video camera 132 provides video input of the driver's face, the red LED 138 is within the driver's normal field of vision, and the buzzer 134 and the speaker 136 are audible to the driver.

Figure 4:
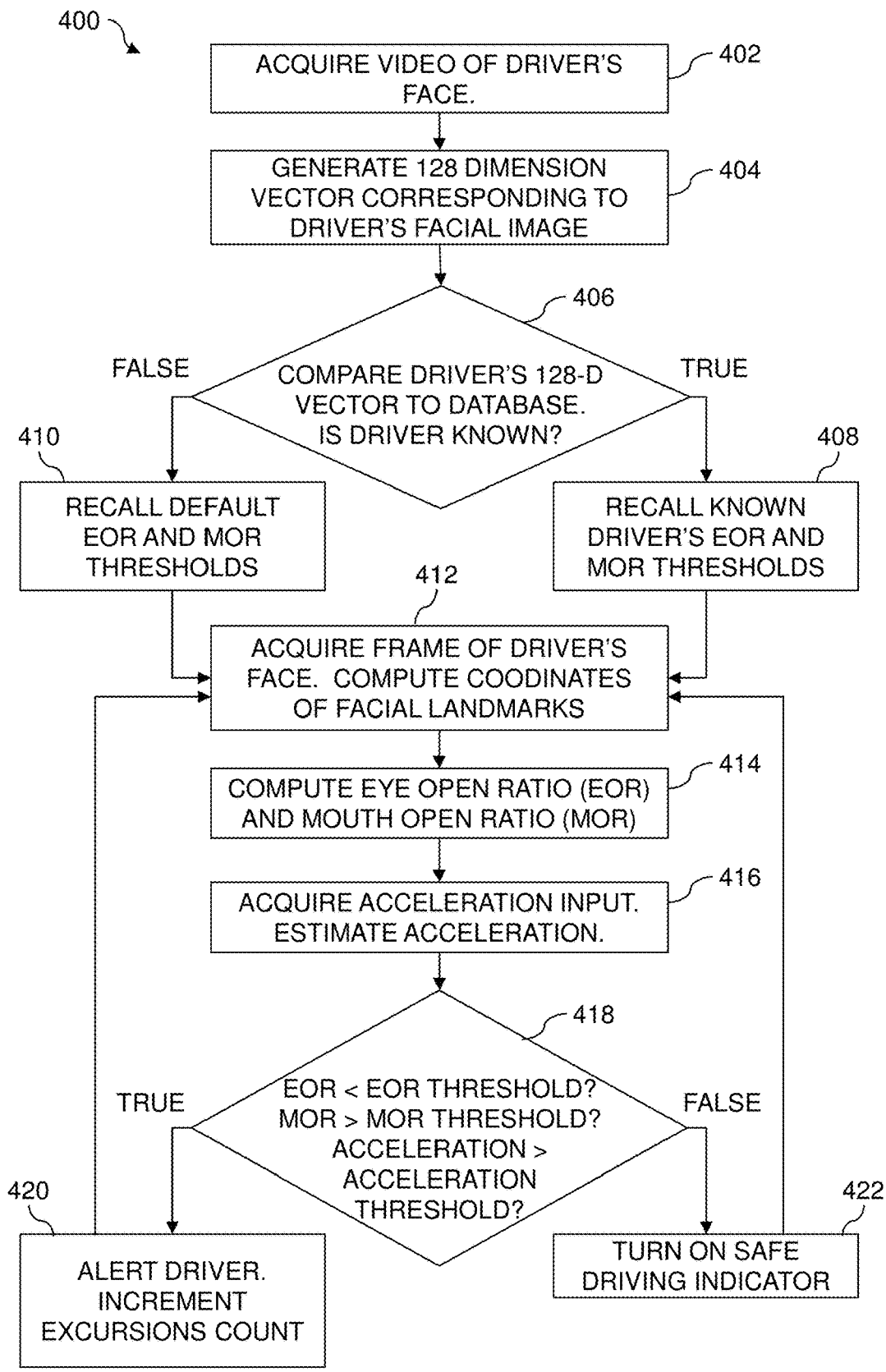
FIG. 4 is a flowchart of an example method of operation of the distracted driver detection device.

FIG. 4 is a flowchart of an example method of operation of the distracted driver detection device. The method 400 begins with step 402, which is to acquire video input of the driver's face. The video input is acquired by the processor 102 from the video camera 132, of FIG. 1. One or more frames of the driver's face may be acquired in step 402.

Step 404 of the method 400 is to generate a 128-d vector corresponding to the driver's facial image. The 128-d vector is generated as disclosed above using the encode_faces.py routine in Dlib.

Step 406 of the method 400 is to compare the 128-d vector corresponding to the driver's facial image to the stored 128-d vectors in the driver database. Step 406 continues by determining if the driver is known, by determining if the driver's 128-d vector is sufficiently close to one of the stored 128-d vectors to provide high confidence of a match. If the outcome of step 406 is TRUE, that is, if the driver is known, the method 400 branches to step 408. If the outcome of step 406 is FALSE, that is, if the driver is not known, the method 400 branches to step 410.

Step 408 is to recall stored values for the EOR threshold and the MOR threshold that are specific to the known driver. The stored EOR threshold and the MOR threshold values are used to provide more accurate assessments of distracted driving by the known driver, compared to using standard thresholds. After step 408 is executed, the method 400 continues with step 412.

Step 410 is to recall standard values for the EOR threshold and the MOR threshold for use with the driver. The standard EOR threshold and the MOR threshold values may be calculated as an average of the EOR threshold and the MOR threshold values for the known drivers, or may be estimated from a database of facial images, by way of example. Data taken by the inventor on the EOR indicates a value of 0.21 to 0.23 for the standard EOR threshold is effective in recognizing distracted driving. The EOR data is discussed in more detail in reference to FIG. 6A through FIG. 6D. Data taken by the inventor on the MOR indicates a value of 0.57 to 0.61 for the standard MOR threshold is effective in recognizing distracted driving. The MOR data is discussed in more detail in reference to FIG. 7. Other methods for generating the EOR threshold and the MOR threshold values are within the scope of this example method 400. After step 410 is executed, the method 400 continues with step 412.

Step 412 is for the processor 102 to acquire at least one frame of the driver's face from the video input provided by the video camera 132. The processor 102 then calculates the facial landmarks coordinates as disclosed above, using the Haar cascade routine.

The method 400 continues with step 414, which is for the processor 102 to compute the EOR value and the MOR value for the current frame of the driver's face, using the facial landmarks coordinates that were calculated in step 412.

Figure 5A:
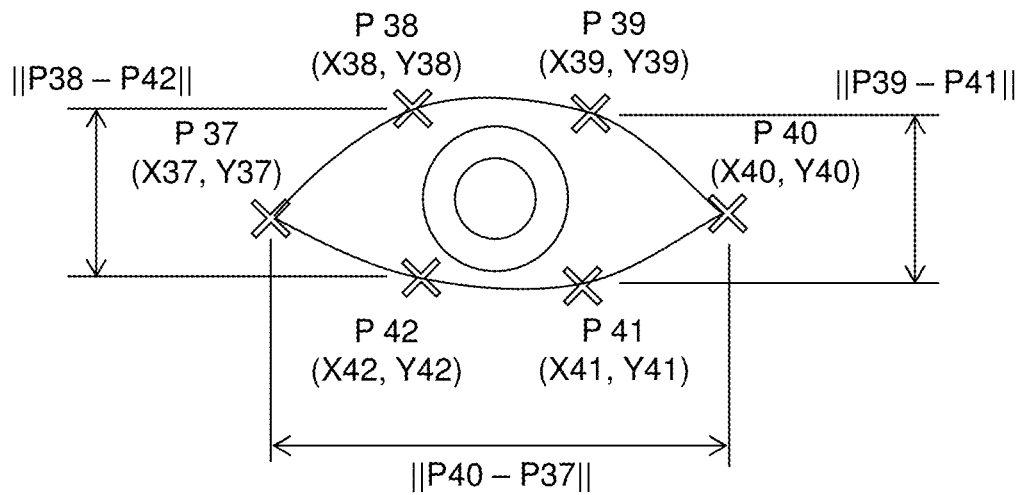
FIG. 5A shows the facial landmarks P37 through P42 for the right eye in detail.

The EOR is computed as an average of a right EOR for the right eye shape structure and a left EOR for the left eye shape structure. The right EOR uses the facial coordinates for the right eye, namely, the coordinates for the facial landmarks P37 through P42, denoted $(x_{37}, y_{37})$ through $(x_{42},$ $y_{42}$). FIG. 5A shows the facial landmarks P37 through P42 for the right eye in more detail. The right EOR is calculated as an average of vertical openings of the right eye shape structure, divided by a horizontal opening of the right eye shape structure. The vertical openings of the right eye are calculated as ‖P38–P42‖ and ‖P39–P41‖, as depicted in FIG. 5A, where the parallel brackets indicates the distance between the facial landmarks specified. In terms of the coordinates:

$$\|P38-P42\|=\sqrt{(x_{38}-x_{42})^2+(y_{38}-y_{42})^2}.$$

The horizontal opening of the right eye is calculated as ‖P40–P37‖, as depicted in FIG. 5A. Thus, the right EOR is calculated as:

$$\frac{\|P38-P42\|+\|P39-P41\|}{2\times\|P40-P37\|}.$$

Figure 5B:
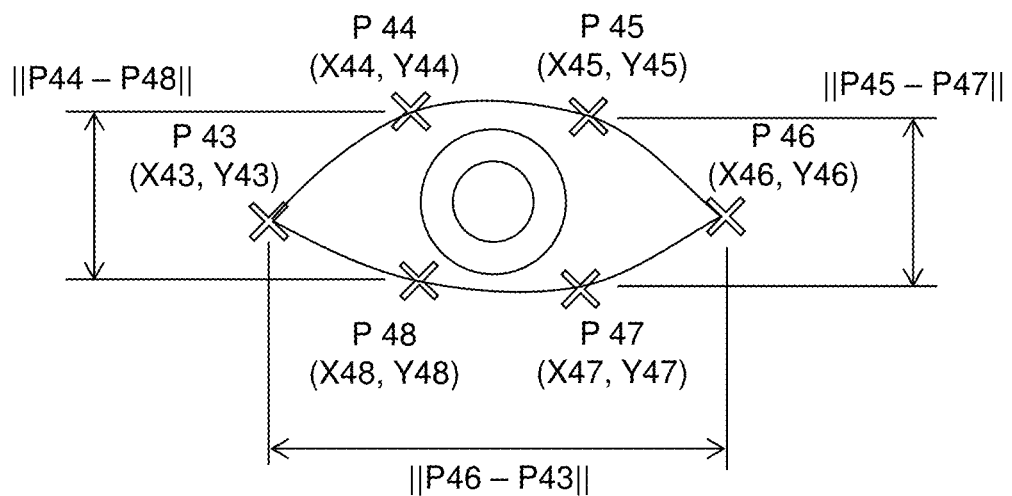
FIG. 5B shows the facial landmarks P43 through P48 for the left eye in detail.

The left EOR uses the facial coordinates for the left eye, namely, the coordinates for the facial landmarks P43 through P48. FIG. 5B shows the facial landmarks P43 through P48 for the left eye in more detail. The left EOR is calculated as an average of vertical openings of the left eye shape structure, divided by a horizontal opening of the left eye shape structure. The left EOR is calculated as:

$$\frac{\|P44-P48\|+\|P45-P47\|}{2\times\|P46-P43\|}.$$

Figure 5C:
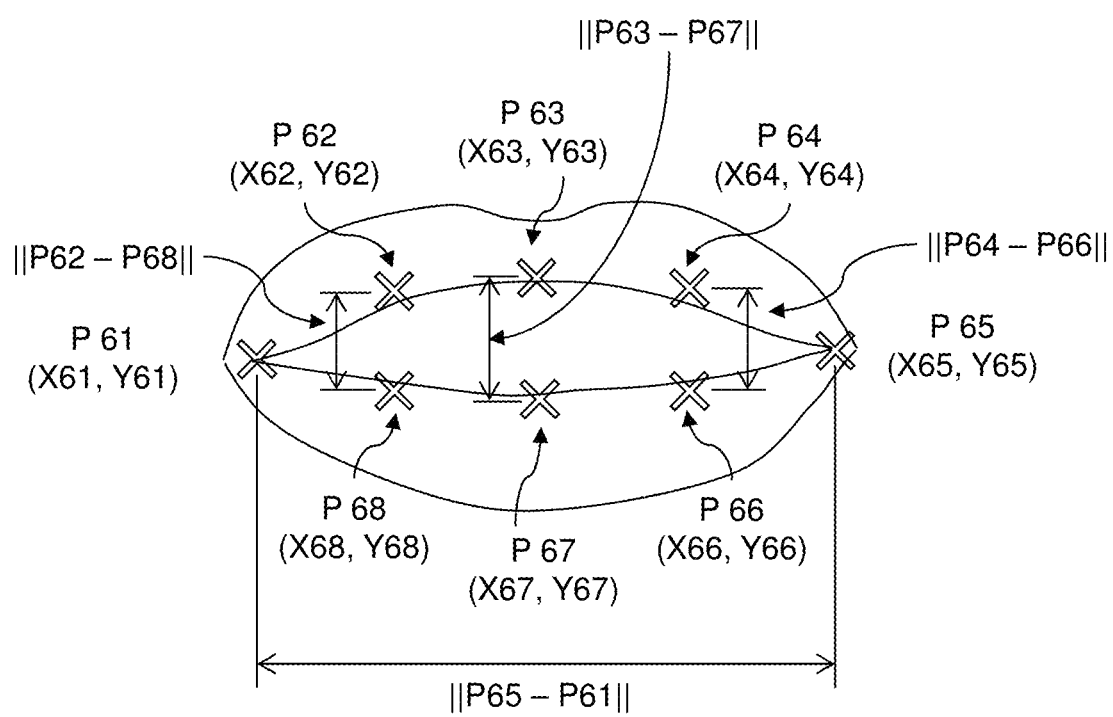
FIG. 5C shows the facial landmarks P61 through P68 for the mouth in detail.

The MOR uses some of the facial coordinates for the mouth, namely, the coordinates for the facial landmarks P61 through P68. FIG. 5C shows the facial landmarks P61 through P68 for the mouth in more detail. The MOR is calculated as a vertical opening of the mouth, divided by a horizontal opening of the mouth. The horizontal opening of the mouth is calculated as ‖P61–P65‖. The vertical opening of the mouth may use any combination of the vertical extents ‖P62–P68‖, ‖P63–P67‖, and ‖P64–P66‖, as depicted in FIG. 5C. The vertical opening of the mouth may be calculated using any of three formulae:

$$\frac{\|P62-P68\|+\|P63-P67\|+\|P64-P66\|}{3}, \quad \text{Formula 1}$$

$$\frac{\|P62-P68\|+\|P64-P66\|}{2}, \text{ or} \quad \text{Formula 2}$$

$$\|P63-P67\|. \quad \text{Formula 3}$$

Accordingly, the MOR may be calculated by any of the following:

$$\frac{\|P62-P68\|+\|P63-P67\|+\|P64-P66\|}{3\times\|P61-P65\|}, \quad \text{MOR 1}$$

$$\frac{\|P62-P68\|+\|P64-P66\|}{2\times\|P61-P65\|}, \text{ or} \quad \text{MOR 2}$$

$$\frac{\|P63-P67\|}{\|P61-P65\|}. \quad \text{MOR 3}$$

The distracted driver detection device 100 implements MOR 3 in step 414.

Referring back to FIG. 4, the method 400 continues with step 416, which is for the processor 102 to acquire the acceleration input from the accelerometer 142 of FIG. 1. The acceleration input may be provided in a numerical format corresponding to a commonly used set of units, such as meters/second$^2$, or may be provided in arbitrary units. The processor 102 converts the acceleration input to an estimate of the acceleration of the vehicle.

The method 400 continues with step 418, which is a decision step having three criteria. The first criterion is that the EOR value obtained in step 414 is less than the EOR threshold for consecutive frames during a prescribed EOR assessment time. The distracted driver detection device 100 is configured to implement the EOR assessment time as 8 consecutive frames of the video input, that is, 400 milliseconds at a frame rate of 20 frames per second. For the first criterion, the EOR value obtained in step 414 is compared to the EOR threshold provided in step 408 or step 410. If the EOR value obtained in step 414 is less than the EOR threshold for 8 consecutive frames, the first criterion is met and the result of step 418 is TRUE.

The second criterion is that the MOR value obtained in step 414 is greater than the MOR threshold for consecutive frames during a prescribed MOR assessment time. The distracted driver detection device 100 is configured to implement the MOR assessment time as 10 consecutive frames of the video input, that is, 500 milliseconds at a frame rate of 20 frames per second. For the second criterion, the MOR value obtained in step 414 is compared to the MOR threshold provided in step 408 or step 410. If the MOR value obtained in step 414 is greater than the MOR threshold for 10 consecutive frames, the second criterion is met and the result of step 418 is TRUE.

For the third criterion, the estimate of the acceleration provided in step 416 is compared to the acceleration threshold. Research done on safe braking and safe acceleration has shown that an appropriate value for the acceleration threshold is 0.5 g, that is 4.9 meters/second$^2$, wherein g is the acceleration due to gravity on Earth, or 9.81 meters/second$^2$. If the estimate of the acceleration provided in step 416 is greater than the acceleration threshold, the third criterion is met and the result of step 418 is TRUE. The result of step 418 is determined with regard to the three criteria independently; if any of the three criteria is met, the result of step 418 is TRUE. If none of the three criteria is met, result of step 418 is FALSE.

If the result of step 418 is TRUE, the method 400 branches to step 420. If the result of step 418 is FALSE, the method 400 branches to step 422.

Step 420 is to alert the driver that indications of distracted driving have been detected by the distracted driver detection device 100. To alert the driver, the processor 102 provides the audio alert signal to the audio alert component of the distracted driver detection device 100 and provides the visual alert signal to the visual alert component. In the manifestation of the distracted driver detection device 100 disclosed in reference to FIG. 1, the processor 102 provides the first audio alert signal through the GPIO port 126 to the buzzer 134, and provides the second audio alert signal through the audio/visual jack 118 to the speaker 136. The first audio alert signal causes the buzzer 134 to emit a buzzing sound to alert the driver. The second audio alert signal causes the speaker 136 to emit an audio message, such as "Distracted driving detected" or "Eyes on the road, please". Other implementations of the audio message are within the scope of this example. The audio alert signal may be implemented as a pre-recorded audio signal, or may be generated by a text-to-speech routine by the processor 102.

To further alert the driver that indications of distracted driving have been detected, the processor 102 provides the visual alert signal to the visual alert component, which is manifested as the red LED 138. The visual alert signal causes the red LED 138 to emit red light within the driver's normal field of view. The red light may be steady for a prescribed time, or may be flashing for the prescribed time.

Step 420 further includes incrementing an excursion count of excursions of the EOR threshold excursions, MOR threshold excursions, and acceleration threshold excursions. If the excursion count exceeds a prescribed limit within a defined monitor time period, the processor 102 reports the excursion count using the wireless communication component 110 to a receiver that is external to the distracted driver detection device 100. The excursion count may be reported to a cellphone in the vehicle, for example, and may be relayed to a monitoring party external to the vehicle, such as an owner of the vehicle. After step 420 is executed, the method 400 branches to step 412 to continue monitoring for distracted driving.

In step 422, the processor 102 provides the safe driving signal to the safe driving visual signal component, implemented as the green LED 140 of the distracted driver detection device 100. The green LED 140 emits green light, signaling to the driver that no indication of distracted driving are currently detected. After step 422 is executed, the method 400 branches to step 412 to continue monitoring for distracted driving. The method 400 continues until the processor 102 is turned off, for example, by turning off the vehicle electrical system after driving is completed.

Figure 6A:
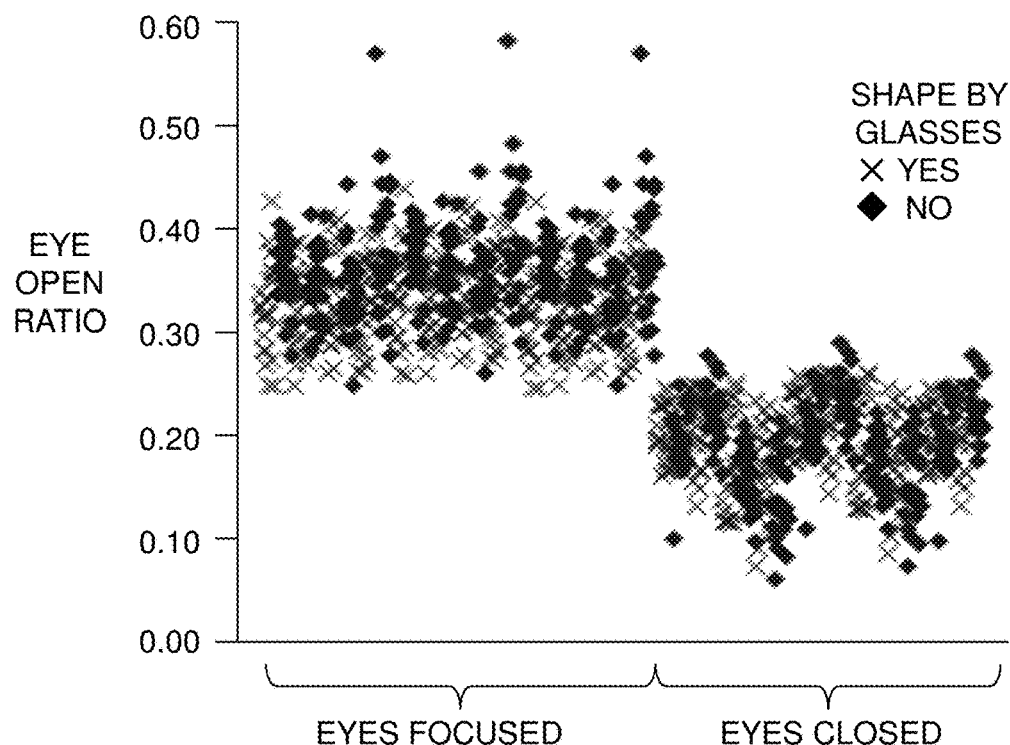
FIG. 6A through FIG. 6D show data that was collected by the inventor on the eye open ratio (EOR) for various individuals, in pursuit of this invention.

FIG. 6A through FIG. 6D show data that was collected by the inventor on the EOR for various individuals, in pursuit of this invention. Referring to FIG. 6A, EOR values were measured with the individuals' eyes focused and measured again with the eyes closed. Eyeglasses were worn in a portion of these measurements. Each individual's values are plotted in FIG. 6A on a separate vertical column. The data shown in FIG. 6A indicates an EOR threshold of 0.21 to 0.23 is effective for determining if the driver's eyes are closed in at least 95 percent of cases, regardless of whether or not the driver is wearing eyeglasses.

Figure 6B:
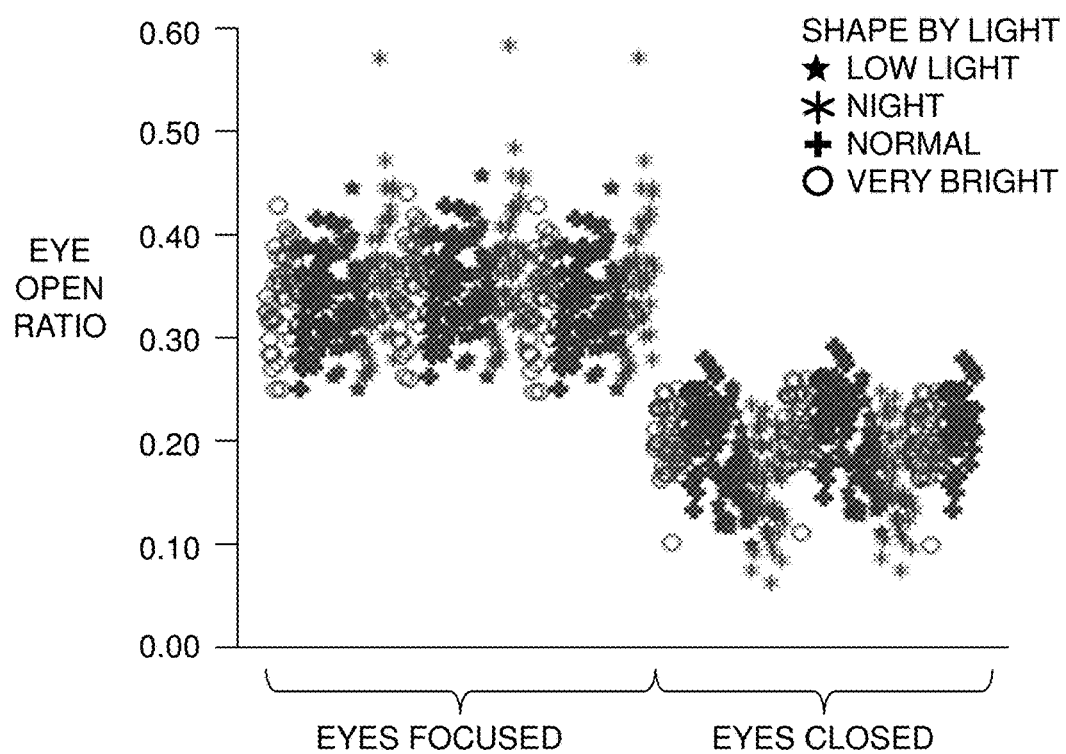

Referring to FIG. 6B, EOR values were measured with the individuals' eyes focused and measured again with the eyes closed, in low light conditions such as driving during dusk, night driving conditions, normal lighting conditions such as driving during daytime, and very bright lighting conditions such as driving with full sun on the driver. Each individual's values are plotted in FIG. 6B on a separate vertical column. The data shown in FIG. 6B indicates an EOR threshold of 0.21 to 0.23 is effective for determining if the driver's eyes are closed in at least 95 percent of cases, in all lighting conditions.

Figure 6C:
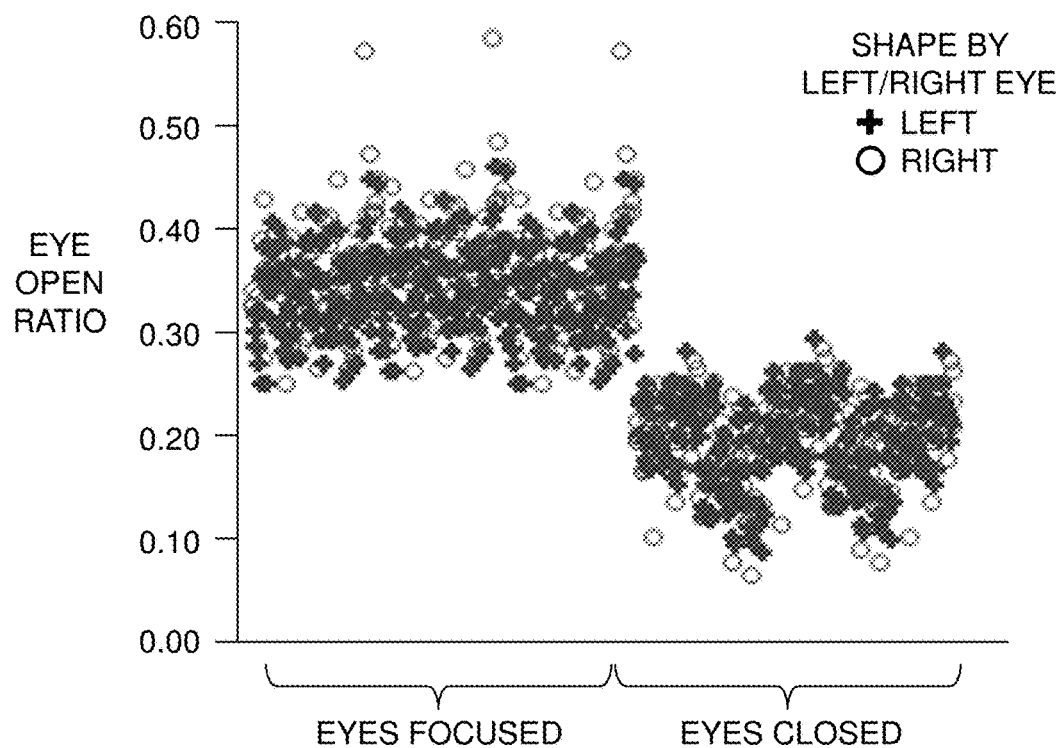

Referring to FIG. 6C, EOR values were measured with the individuals' eyes focused and measured again with the eyes closed. The data in FIG. 6C shows values of the EOR for the individuals' left eyes and the individuals' right eyes, separately. Each individual's values are plotted in FIG. 6C on a separate vertical column. The data shown in FIG. 6C indicates an EOR threshold of 0.21 to 0.23 is effective for determining if the driver's eyes are closed in at least 95 percent of cases, for both left eyes and right eyes.

Figure 6D:
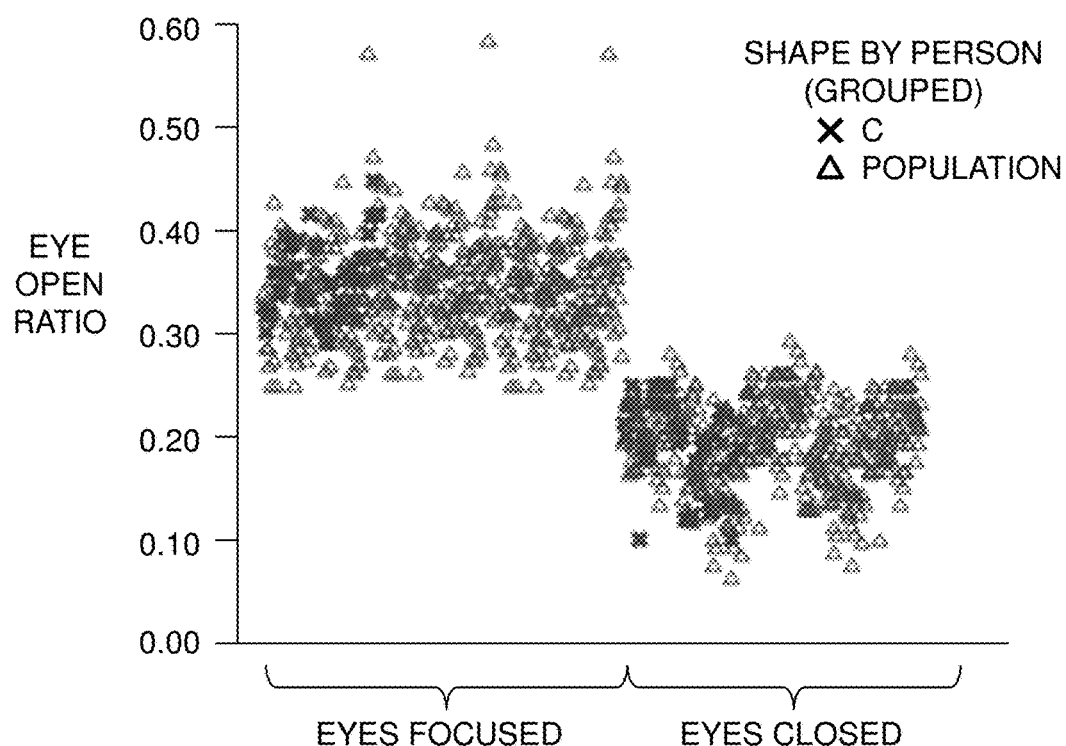

Referring to FIG. 6D, EOR values for an individual, denoted as "C" in FIG. 6D, plotted with EOR values of the population of the individuals measured in the EOR tests. The EOR values for the population indicate an EOR threshold of 0.21 to 0.23 is effective for determining if the driver's eyes are closed in at least 95 percent of cases, while the EOR values for the individual "C" indicate an EOR threshold of 0.255 is more effective for determining if the individual "C" has his/her eyes closed. Thus, the distracted driver detection device 100 may store a standard EOR threshold of 0.21 to 0.23, for example 0.22, for unrecognized drivers, and store a specific EOR threshold of 0.255 for the individual "C", and may recall the stored specific value when the individual "C" is recognized as the driver, as disclosed in reference to the method 400 of FIG. 4.

Figure 7:
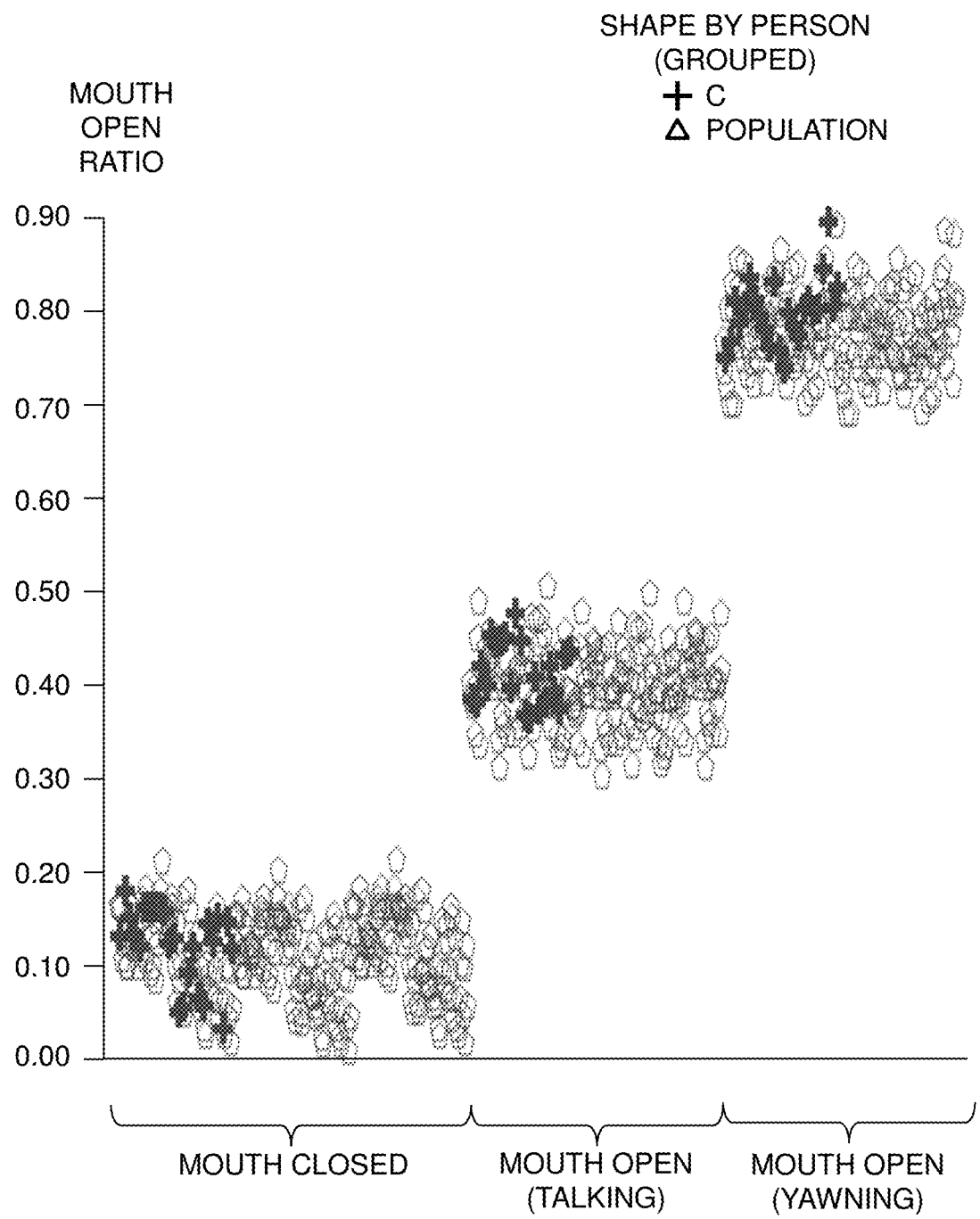
FIG. 7 shows data that was collected by the inventor on the mouth open ratio (MOR) for various individuals, in pursuit of this invention.

FIG. 7 shows data that was collected by the inventor on the MOR for various individuals, in pursuit of this invention. MOR values were measured with the individuals' mouths closed, open while talking, and open while yawning. Yawning is an indicator of distracted driving. The MOR values show clear, distinct ranges for the three modes of mouth status, allowing the distracted driver detection device 100 to distinguish between talking and yawning in at least 99 percent of cases. In FIG. 7, MOR values for an individual, denoted as "C" in FIG. 7, plotted with MOR values of the population of the individuals measured in the MOR tests. The MOR values for the population indicate an MOR threshold of 0.57 to 0.61 is effective for determining if the driver is yawning, while the MOR values for the individual "C" indicate an MOR threshold of 0.60 to 0.64, for example 0.62, is slightly more effective for determining if the individual "C" is yawning. Thus, the distracted driver detection device 100 may store a specific MOR threshold of 0.62 for the individual "C", and may recall the stored specific value when the individual "C" is recognized as the driver, as disclosed in reference to the method 400 of FIG. 4.

While various embodiments of the present disclosure have been described above, it should be understood that they have been presented by way of example only and not limitation. Numerous changes to the disclosed embodiments can be made in accordance with the disclosure herein without departing from the spirit or scope of the disclosure. Thus, the breadth and scope of the present invention should not be limited by any of the above described embodiments. Rather, the scope of the disclosure should be defined in accordance with the following claims and their equivalents.

What is claimed is:

1. A distracted driver detection device, comprising:
a processor including a central processing unit (CPU), random access memory (RAM) containing volatile memory, and a secure digital (SD) card containing non-volatile memory;
a video camera configured to provide video input to the processor;
an accelerometer configured to provide acceleration input to the processor;
a visual alert component, the visual alert component being configured to generate a visual alert upon receiving a visual alert signal from the processor;
an audio alert component, the audio alert component being configured to generate an audio alert upon receiving an audio alert signal from the processor; and
a wireless communication component connected to the processor, the wireless communication component being configured to provide a wireless message upon receiving a wireless alert signal from the processor;
wherein the SD card contains instructions including Open-Source Computer Vision Library (OpenCV) and Dlib, executable by the CPU, which configure the processor to:

identify a left eye shape structure of a driver using the video input, the left eye shape structure including at least 6 facial landmarks;

identify a right eye shape structure of a driver using the video input, the right eye shape structure including at least 6 facial landmarks;

compute an eye open ratio (EOR) as an average of a left EOR of the left eye shape structure and a right EOR of the right eye shape structure;

identify a mouth shape structure of a driver using the video input, the mouth shape structure including at least 20 facial landmarks;

compute a mouth open ratio (MOR) using the mouth shape structure;

generate an estimate of an acceleration using the acceleration input;

provide the audio alert signal to the audio alert component and provide the visual alert signal to the visual alert component when the EOR is less than an EOR threshold for consecutive frames in a prescribed EOR assessment time;

provide the audio alert signal to the audio alert component and provide the visual alert signal to the visual alert component when the MOR is greater than an MOR threshold for consecutive frames in a prescribed MOR assessment time;

provide the audio alert signal to the audio alert component and provide the visual alert signal to the visual alert component when the estimate of the acceleration is greater than an acceleration threshold; and provide the wireless alert signal to the wireless communication component when the processor has provided at least three of the audio alert signals.

2. The distracted driver detection device of claim 1, wherein the processor is a Raspberry Pi microcontroller.

3. The distracted driver detection device of claim 1, wherein the EOR threshold is 0.21 to 0.23.

4. The distracted driver detection device of claim 1, wherein the prescribed EOR assessment time is 400 milliseconds.

5. The distracted driver detection device of claim 1, wherein the MOR threshold is 0.57 to 0.61.

6. The distracted driver detection device of claim 1, wherein the prescribed MOR assessment time is 500 milliseconds.

7. The distracted driver detection device of claim 1, wherein the acceleration threshold is 4.9 meters/sec2.

8. The distracted driver detection device of claim 1, wherein the video camera is configured to provide the video input at a frame rate of 15 to 30 video frames per second.

9. The distracted driver detection device of claim 1, wherein the video camera is configured to provide 640×480 pixel frames in the video input.

10. The distracted driver detection device of claim 1, wherein the instructions configure the processor to generate 128 dimension (128 d) vectors that are representative of individual faces using a Histogram of Oriented Gradients (HOG) algorithm.

11. The distracted driver detection device of claim 1, wherein the instructions configure the processor to recognize a specific face using a program encode_faces.py in Dlib.

12. The distracted driver detection device of claim 1, wherein the instructions configure the processor to generate the facial landmarks using a Haar cascade face detector in Dlib.

13. The distracted driver detection device of claim 1, wherein the left EOR is calculated as an average of vertical openings of the left eye shape structure, divided by a horizontal opening of the left eye shape structure, and the right EOR is calculated as an average of vertical openings of the right eye shape structure, divided by a horizontal opening of the right eye shape structure.

14. The distracted driver detection device of claim 1, wherein the MOR is calculated as a vertical opening of the mouth shape structure, divided by a horizontal opening of the mouth shape structure.

15. The distracted driver detection device of claim 1, wherein the instructions configure the processor to accumulate an excursion count of EOR threshold excursions, MOR threshold excursions, and acceleration threshold excursions.

16. The distracted driver detection device of claim 15, wherein the instructions configure the processor to report the excursion count using the wireless communication component, when the excursion count exceeds 20 in a 60 minute time period.

17. The distracted driver detection device of claim 1, wherein:
the audio alert component is a first audio alert component;
the audio alert signal is a first audio alert signal;
the first audio alert component is a buzzer configured to generate a buzzer alert upon receiving the first audio alert signal from the processor; and
the distracted driver detection device includes a second audio alert component, the second audio alert component being a speaker configured to generate a voice alert upon receiving a second audio alert signal from the processor.

18. The distracted driver detection device of claim 1, further including a safe driving visual signal component configured to generate a safe driving status signal upon receiving a safe driving signal from the processor, and wherein the instructions configure the processor to provide the safe driving signal when the EOR is below the EOR threshold, the MOR is below the MOR threshold, and the acceleration is below the acceleration threshold.

* * * * *